United States Patent
Janzen et al.

[11] Patent Number: 5,922,024
[45] Date of Patent: Jul. 13, 1999

[54] SOFT TISSUE IMPLANT

[75] Inventors: Ernst Janzen, Laren; Matthias Johannes Hoekstra, Amstelveen; Richard P. Dutrieux, Amsterdam; Leonardus Hermannus Hendrikus Olde Damink, Vaals, all of Netherlands

[73] Assignee: Datascope Investment Corp., Montvale, N.J.

[21] Appl. No.: 08/854,629

[22] Filed: May 12, 1997

Related U.S. Application Data

[62] Division of application No. 08/116,587, Sep. 7, 1993, Pat. No. 5,676,698

[51] Int. Cl.⁶ ........................................... A61F 2/12
[52] U.S. Cl. ........................................... 623/8
[58] Field of Search ........................................... 623/8

[56] References Cited

U.S. PATENT DOCUMENTS

| | | | |
|---|---|---|---|
| 4,291,013 | 9/1981 | Wahlig | 623/11 |
| 4,298,998 | 11/1981 | Naficy | 3/36 |
| 4,474,763 | 10/1984 | Lubowe | 514/21 |
| 4,582,640 | 4/1986 | Smestad et al. | 260/123.7 |
| 4,597,762 | 7/1986 | Walter et al. | 623/8 |
| 4,600,533 | 7/1986 | Chu | 530/356 |
| 4,601,896 | 7/1986 | Nugent | 424/21 |
| 4,655,980 | 4/1987 | Chu | 264/102 |
| 4,689,399 | 8/1987 | Chu | 530/356 |
| 4,725,671 | 2/1988 | Chu et al. | 530/356 |
| 4,772,284 | 9/1988 | Jefferies et al. | 623/8 |
| 4,801,299 | 1/1989 | Brendel et al. | 623/7 |
| 4,840,628 | 6/1989 | Cavon | 623/8 |
| 5,002,071 | 3/1991 | Harrel | 623/66 |
| 5,094,661 | 3/1992 | Levy et al. | 8/94.11 |
| 5,206,028 | 4/1993 | Li | 424/484 |
| 5,219,360 | 6/1993 | Georgiade | 623/11 |
| 5,219,576 | 6/1993 | Chu et al. | 424/484 |
| 5,397,353 | 3/1995 | Oliver et al. | 623/11 |
| 5,523,291 | 6/1996 | Janzen et al. | 514/21 |

FOREIGN PATENT DOCUMENTS

| 1565340 | 4/1980 | United Kingdom | 623/11 |
|---|---|---|---|

OTHER PUBLICATIONS

Brochure entitled "Toothed Colloid Mill MZ", FRYMA, Jan. 1983.

"Hackh's Chemical Dictionary", cover, first sheet, p. 171 (1969).

Thomas Register of American Manufacturers, vol. 8, pp. MIL15930–31 (1990).

Cronin, T., "Silicone Breast Implant", chapter 36 of "Biomaterials in Reconstructive Surgery", Rubin, L., ed., pp. 552–563 (1983).

*Primary Examiner*—Robert A. Clarke
*Assistant Examiner*—Catherine Cogut
*Attorney, Agent, or Firm*—Fitzpatrick, Cella, Harper & Scinto

[57] ABSTRACT

Soft tissue implants can be constructed by forming an outer membrane into a closed pouch and filling material in that pouch. A composition for use as a filler material in such a soft tissue implant may include elastin and collagen. The filling material has collagen as a component thereof, and this collagen can be cross-linked or not cross-linked. Methods of making such implants are described.

11 Claims, 1 Drawing Sheet

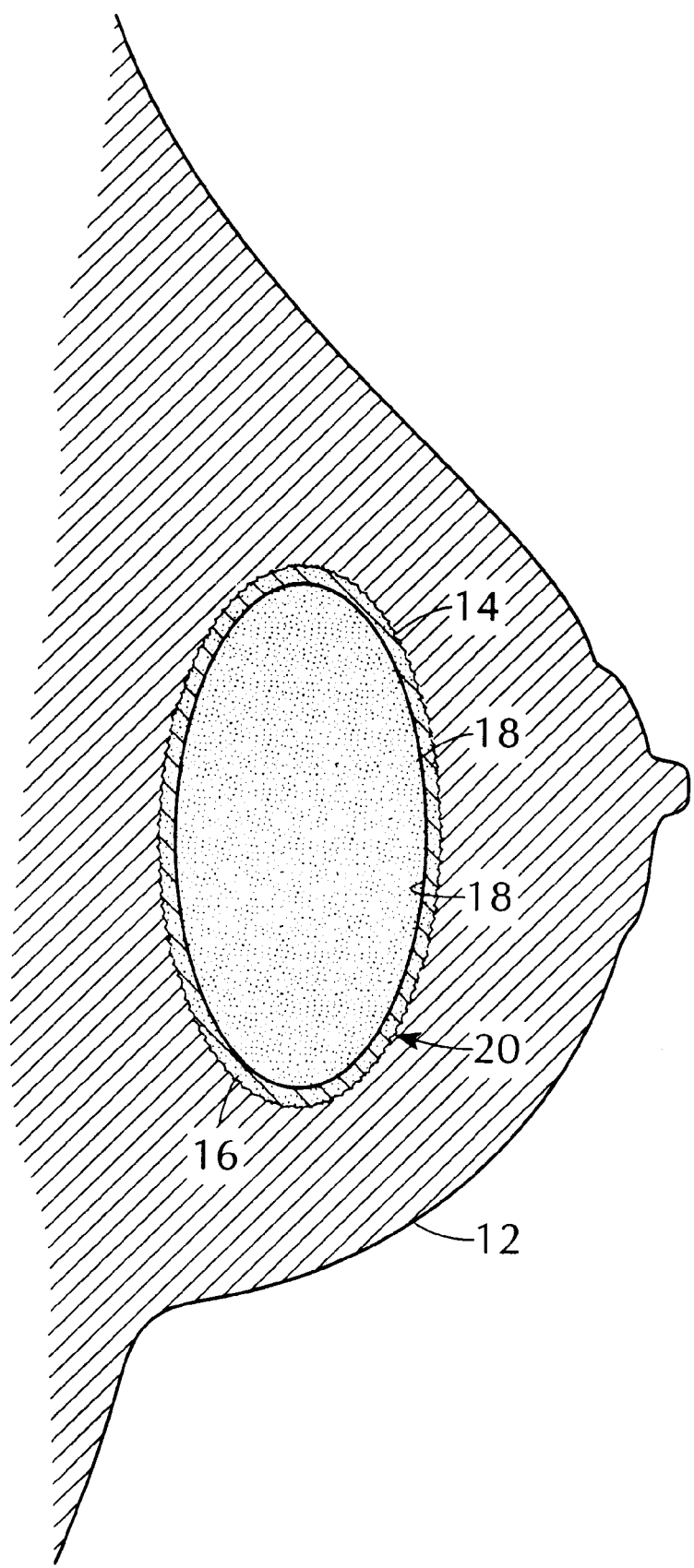

SOFT TISSUE IMPLANT

This application is a division of application Ser. No. 08/116,587, filed Sep. 7. 1993, now U.S. Pat. No. 5,676,698.

BACKGROUND OF THE INVENTION

1. Field of the Invention

The present invention relates to soft tissue implants, often referred to as prostheses. Such implants have particular utility for breast augmentation and breast reconstruction.

2. Related Background

Over the years, many attempts have been made to develop prostheses suitable for breast implants.

At first, breast augmentation was accomplished by means of injecting liquids, primarily silicone gel, directly into the soft tissue of the breast. That silicone gel, however, was soon found to migrate, causing serious medical problems. To solve the migration problem, the next step was to encapsulate the silicone gel in a pouch or envelope made of some impervious material, often silicone, and then surgically implant the pouch in the breast.

Unfortunately, that approach brought with it a new set of problems. It was soon found that the body's defense mechanisms cause the formation of a natural tissue capsule around the breast prosthesis thereby enclosing and isolating it from the surrounding body tissue. This fibrous tissue capsule, containing fibroblasts, myofibroblasts and inflammatory cells, has a continuous tendency to contract, thereby tightening around the implant and causing it to become very firm. Contracture can also lead to tenderness of the breast, pain, erosion of the adjacent tissue as well as other complications.

To further exacerbate the problem, studies have shown that the silicone gel fillers found in many breast prosthesis tend to "bleed" through the membrane envelope causing a chronic inflammatory response in the surrounding tissue. This chronic inflammatory response also leads to natural tissue encapsulation and eventually to contracture.

Numerous attempts have been made to overcome the contracture problem. For example, U.S. Pat. No. 4,298,998 proposes using a double walled or "dual lumen" prosthesis with an absorbable outer wall and an absorbable filler material between the inner and outer walls. U.S. Pat. No. 4,772,284 proposes using a more biocompatible filler material, for example, collagen gels and saline. U.S. Pat. No. 4,840,628 describes a prosthesis that has neither a liquid core nor a permanent enclosing membrane. Instead, it suggests using a cast silicone gel elastomer having a homogeneous cohesive structure throughout. In addition, that casting may be covered with a minimum membrane coating or an absorbable shell.

The present invention addresses the encapsulation/contracture/inflammatory response problems by using all natural materials rather than silicone or the like.

SUMMARY OF THE INVENTION

The soft tissue implant of the present invention is comprised of an envelope or pouch, defined by a thin membrane, and a filler. The envelope membrane is made of a collagen/elastin matrix of natural origin and the filler is made of elastin and collagen fibers. The native matrix is more than a scaffold alone and maintains a dynamic relationship with the ingrowing cells.

As used herein, the term "elastin" is intended to encompass protein elastin as well as the combination of elastin with microfibrils, which combination is often referred to in the technical literature as elastic fibers.

The envelope membrane is preferably derived from animal membrane which has been cleaned of non-collagenous and non-elastinous proteins. Because it contains only natural materials, materials which, in their cleaned states, are non-antigenic or only minimally antigenic, the membrane does not cause the kind of chronic inflammatory response which is common with artificial materials such as silicone. As a result, a chronic tissue reaction and encapsulation does not occur and there is no contracture with which to be concerned.

Similarly, the filler material is composed of natural materials, namely, cleaned collagen and elastin fibers, without any cross-linking agents. Since the filler is comprised of non-antigenic or only minimally antigenic materials, "bleeding" of the filler material through the membrane is of no concern. Hence, neither the membrane nor the filler is likely to cause a chronic inflammatory reaction and tissue encapsulation with contracture.

Preferred animal tissue starting materials for the envelope membrane include the peritoneum and omentum. Other suitable membrane starting materials include other natural membranes such as amnion, chorion, pleura, pericardium, facia lata, dura mater, intestine or dermis. While these membranes can be obtained from many animal species, the most readily available are membranes of bovine, porcine or ovine origin.

The filling material may be derived from ligaments, tendons or membranes, commonly of bovine, porcine or ovine origin. The preferred starting material for making the filler for use in the present invention is the bovine ligamentum nuchae because of its high elastin content.

A further aspect of this invention involves a method of making a soft tissue implant pouch containing filling material wherein the pouch is made from peritoneum, omentum, amnion, chorion, pleura, pericardium, facia lata, dura mater, intestine or dermis and the filling material is derived from one of the following starting materials, animal ligaments, membranes and tendons. This method involves treating the natural animal membrane, treating the filling material before, after or simultaneously with treating the natural animal membrane, forming the treated animal membrane into a partially closed pouch, placing the treated filling material into the partially closed pouch and then closing the rest of the pouch.

If desired, the pouch can be made of a single piece of treated natural animal membrane which has been folded and sewn around the periphery of the pouch.

DESCRIPTION OF THE DRAWINGS

FIG. 1 is a section through a female breast showing a soft tissue implant according to the present invention.

DETAILED DESCRIPTION

FIG. 1 depicts a soft tissue implant 10 according to the present invention having been implanted in a female breast 12. The implant or prosthesis 10 is comprised of an envelope or pouch 14 and filler material 16. The filler material is comprised primarily of collagen and elastin fibers whereas the pouch is made of an elastin/collagen membrane derived from natural animal tissue.

Preferred pouch membrane starting materials include bovine or porcine peritoneum or omentum. These tissues are cleaned of non-collagenous and non-elastinous proteins by a process which does not destroy the natural collagen/elastin matrix. One suitable cleaning method is described in U.S.

Pat. No. 5,028,695, the disclosure of which is incorporated herein by reference.

Basically, the cleaning process is carried out by first washing the membranes and subjecting them to a strong alkali treatment, preferably by soaking them in a sodium hydroxide (NaOH) solution. Other suitable alkali treatments might include potassium hydroxide (KOH) or calcium hydroxide (CaOH). After washing again with water, the membranes are treated with a strong acid, preferably hydrochloric acid (HCl). Other suitable acids might include sulfuric acid ($H_2SO_4$) and acetic acid ($C_2H_4O_2$). Washing then removes most of the acid, and that which remains is neutralized by use of a base, preferably bicarbonate of soda ($NaHCO_3$). Other suitable neutralizing agents might include sodium acetate ($NaC_2H_3O_2$) and disodium hydrogen phosphate. The resulting salts are then removed by washing in water, following which the water is removed, for example, by acetone extractions, and the membranes are air dried to remove the residual acetone.

While it is believed unnecessary and, indeed, preferable not to cross-link the collagen in the pouch membrane, cross-linking may be used for some applications, for example, it is possible that some cross linking may assist in decreasing the degradation rate. If there is to be cross-linking, the cross-linked collagen should be non-cytotoxic and should not provoke cellular or immune responses. Hexamethylene diisocyanate may be one such cross-linking agent, as may some polyepoxy compounds, for example, polyethylene glycol diglycidyl ether and water soluble carbodiimides, for example, 1-ethyl-3[3-dimethyl amino propyl]carbodiimide.HCl in the presence of N-hydroxysuccinimide. Since the cross-linking agents are believed to form very stable bonds with the collagen, they produce cross-linked collagen which is non-cytotoxic and is not likely to provoke any immune or cellular response.

Preferred filler starting materials include ligaments and tendons. In particular, the starting material believed to be most suitable is bovine ligamentum nuchae because it is made up largely of elastin, with only a relatively small amount of collagen. Indeed, more than 70% of the dry weight of this ligament is elastin. The relatively high elastin content and relatively low collagen content make it an ideal starting material for the filler material of the present invention.

As noted above, the term "elastin" is used herein to include elastin together with microfibrils. Elastin in natural tissue is normally associated with microfibrils and, for the purpose of the present invention, no effort is made to remove the microfibrils. While, in its broadest scope, the present invention covers the use of elastin which has had the microfibrils removed, it is believed preferable not to remove them.

To make a preferred filler material according to the present invention, the ligamentum nuchae may be cleaned using a process similar to that taught in U.S. Pat. No. 5,028,695. The ligament is first cleaned of blood and adherent tissue and then is chemically treated to remove the non-elastinous and non-collagenous components. The chemical treatment preferably includes subjecting the ligament to a strong alkali treatment then to an acid treatment and then to a neutralizing bath. A preferred alkali treatment involves soaking in a sodium hydroxide (NaOH) bath. Other suitable alkali agents include potassium hydroxide and calcium hydroxide. A preferred acid for the acid treatment is hydrochloric acid (HCl) although other acids, such as sulfuric acid and acetic acid, might also be suitable. As for the neutralizing step, many suitable bases are available, the preferred one being bicarbonate of soda ($NaHCO_3$), while other neutralizing agents might include sodium acetate and disodium hydrogen phosphate.

The chemical treatment is followed by mechanical manipulation which separates the elastin and collagen fibers. The separated fibers are then dried, preferably without cross-linking. However, it might be possible to decrease the degradation time if the collagen were cross-linked so as to produce a non-cytotoxic material that does not provoke a cellular or immune response. Suitable cross-linking agents might include a hexamethylene diisocyanate, a polyepoxy compound, or a water soluble carbodiimide as discussed above.

Although the preferred filler starting material is the ligamentum nuchae, other starting materials may also be used. For example, the peritoneum and omentum membranes have about 15% elastin and could also be used to make a filler material in accordance with the present invention. In addition, elastin and collagen from different sources could be mixed together to produce a mix having whatever proportions are deemed advantageous for a particular application. It is believed, however, that the composition should have minimum of perhaps as little as about 10% elastin (dry weight) and might have as much as 90% or perhaps even higher of elastin.

While, as noted, it is believed preferable for the filler to contain both collagen and elastin, elastin alone without collagen might also be suitable. Similarly, collagen without elastin might be used, particularly if that collagen is cross linked with an agent that does not leach out and produces a non-cytotoxic composition that does not provoke a significant immune or cellular response. Such suitable cross-linking agents might include the hexamethylene diisocyanate, polyepoxy compounds and water soluble carbodiimides referred to above.

It has been found that the cleaned membranes prepared in accordance with this invention have a mesothelial side 18 and a loose connective tissue side 20. The pouch 14 is made with the loose connective tissue side facing out because when implanted with the loose connective tissue side out, it is believed that the pouch will rapidly become anchored in place as a result of fibrovascular ingrowth from the surrounding tissue.

Unlike the prior art prosthesis, the implant of the present invention employs a porous membrane to form the envelope. A porous membrane is made possible because the filler material 16 is made up of cleaned natural fibers, namely elastin and collagen, which have very low antigenicity and hence cause only minor and transitory inflammatory response.

In addition to being porous, the envelope membrane has very low antigenicity and produces only a very minor inflammatory response. Moreover, because the loose connective tissue side which faces out promotes vascularization, the membrane quickly becomes integrated into the surrounding tissue without the formation of the fibrous encapsulation and contracture which is found in the prior art.

It is believed that once the prosthesis of the present invention is implanted, the collagen in the membrane causes some mild transitory tissue reaction in the surrounding tissue and, therefore, some increased vascular activity. Vascularization of the implant membrane begins while the collagen in that membrane is being resorbed and proceeds through the membrane and into the collagen/elastin filler material. This vascular ingrowth through the membrane into the filler material leads to resorption of the collagen, both in the membrane matrix and in the filler material.

As vascularization and resorption of the collagen in the filler material is going forward, fibroblasts are activated. Those fibroblasts, which appear to have an affinity for elastin, attach themselves to the elastin fibers and lay down an organized matrix of new native connective tissue.

The natural vascularization which occurs and the integration of the envelope membrane into the surrounding tissue may make suturing of the envelope in place unnecessary. If however, such suturing is deemed advisable, it can easily be done, preferably with non-absorbable suture material like prolene.

In this connection, it should be noted that suturing can be done both easily and without creating any additional risk. The envelope membrane, being composed of a natural elastin/collagen matrix, will readily close any hole made by a needle and suture. Moreover, even if the natural sealing of the holes is not complete, slight leaks of filler material are of no concern because, as discussed above, the filler material is made up of cleaned collagen and elastin, both of which are either non-antigenic or, at worst, only minimally antigenic.

While it is believed most desirable for the membrane to consist of a natural collagen or collagen/elastin matrix, the filler material herein disclosed can be used in any pouch. For example, if it is determined that the primary problem with present day pouches relates to the filler material rather than the pouch membrane material, the filler of the present invention could be substituted for that prior art filler without changing the pouch membrane. Thus, a pouch made of a silicone membrane filled with the filler material of the present invention should be understood as falling within the scope of the present invention.

EXAMPLE 1
Preparation of Membrane

A batch of about 200 porcine peritoneal membranes, each measuring about 20×30 cm are obtained from a slaughterhouse and, if necessary, mechanically freed of fatty residues. These membranes, which weigh about 10 kg, are washed for about 4 hours with running tap water at about 45° C. in a rotating drum and then washed three more times with 40 l. of room temperature tap water.

After the washing steps have been completed, the membranes are soaked in 40 l. of a 0.5% (w/w) solution of sodium hydroxide (NaOH) in tap water for up to 13 days at room temperature until the amido nitrogen content is reduced by about one half to original value or to about 0.35 m mol/g. or less. During this period, the NaOH solution may be refreshed several times. Thereafter, the membranes are again washed 3 times with 40 l. of room temperature tap water.

Next, the membranes are soaked for 4 hours in a room temperature solution of hydrochloric acid (HCl). The HCL solution is prepared by mixing 4 l. of concentrated (37%) HCl with 36 l. of tap water.

After completion of the acid treatment, the membranes are washed with tap water until the pH of the wash water is between 2.5 and 3. The remaining acid is then neutralized by soaking the membranes overnight in 50 l. of tap water to which 350 g. sodium hydrogen carbonate ($NaHCO_3$) has been added.

There then follows another tap water wash to remove the salts formed during neutralization. Samples of the wash water are periodically mixed with a silver nitrate ($AgNO_3$) solution. When mixing with the $AgNO_3$ solution no longer produces precipitates, removal of salts is deemed complete.

Water is then removed from the membranes by means of acetone extractions. Finally, the acetone is removed by air drying while the membranes are kept in constant motion.

EXAMPLE 2
Preparation of Filler Material

A 10 kg batch of bovine ligamentum nuchae which has been mechanically freed of fatty residues is soaked overnight in about 40 l. of tap water at room temperature. This initial soak removes adherent blood and other water soluble components and also assures a more or less natural degree of hydration which is believed to facilitate the subsequent chemical treatments.

The ligaments are then washed twice for about 10 minutes each with 50 l. of tap water, before being placed in 50 l. of a 4% (w/w) solution of sodium hydroxide (NaOH) in tap water. They are permitted to remain in this strongly alkaline soak for 48 hrs. at room temperature.

The alkaline soak is followed by three 10 minute washes in 50 l. of tap water. The ligaments are then subjected to a second alkaline soak, this one in 50 l. of a 2% (w/w) solution of NaOH in tap water at room temperature for 72 hrs. After removal from the second alkaline soak they are washed three more times for 10 minutes in 30 l. of tap water to remove the solubilized components.

Next, the ligaments are placed in a solution of hydrochloric acid (HCl) for about 4 hr. The HCl solution for this soak is prepared by mixing 4 l. concentrated (37%) HCl with 36 l. of tap water. The acid soaked ligaments are then washed in tap water until the pH of the wash water is between about 2.5 and 3.

The ligaments are then placed in an $NaHCO_3$ soak to neutralize the remaining acid. The $NaHCO_3$ soak is prepared by adding 350 gm. of $NaHCO_3$ to 50 l. of tap water. The ligaments are left in this neutralizing bath overnight and then they are again washed in tap water to remove the resulting salts. Washing continues until mixing with a silver nitrate ($AgNO_3$) solution produces no precipitates.

A kolloid mill is then used to separate the natural elastin fibers. Fiber length may also be reduced in the kolloid mill. Acetone extractions are then used to remove the water and, finally, the fibers are air dried in an oven at about 75° C.

The filler material which emerges from this process is a fluffy mass of elastin and collagen fibers. They may be used in that state or they may be compressed and molded to any desired shape.

EXAMPLE 3
Preparation of Envelope or Pouch

Two dried membranes, prepared in accordance with Example 1 above, are cut into circles of about 12 cm. in diameter. The edges are sewn together using prolene suture material to form an envelope or pouch. While non-adsorbable suture material like prolene is thought to be preferable, absorbable sutures like polylactide or polyglycolide may also be suitable.

When the membrane edges are sewn together, one section of the periphery is left unsewn and 30 gm. of filler material, prepared in accordance with Example 2 above, is inserted through the unsewn section. The unsewn section is then sewn shut.

In the examples above, both the membranes and the filler material are dried at the end of the cleaning processes. This facilitates handling during the sewing and filling of the pouch. A pouch made of dry materials is more easily sterilized than is one made of wet components. Also, pouches are more easily stored in the dry state and sterility is more easily maintained over extended periods of time when all the materials are dry. Nevertheless, although drying is preferred before preparation of the implant pouch, it is not absolutely necessary.

Finally, approximately 30 minutes before implant surgery, the sterile, dry pouch is hydrated, for example, in sterile water or phosphate buffered saline. The pouch is then implanted in the wet state.

With implants according to the present invention, even after implantation has been completed, the degree of augmentation can still be changed. For example, if the amount of augmentation is found to be insufficient, additional filling material can be injected into the pouch through an hypodermic needle. For such purpose, the filling material would normally be suspended in a biocompatible carrier such as glycerine and water. Because of the nature of the pouch membrane, the hole made by the needle is self sealing and hence seepage of filling material into the surrounding tissue would be minimal to non-existent. Moreover, since the filling material is non-cytotoxic, whatever seepage that might occur would be of no concern.

Similarly, if the degree of augmentation is too great, an hypodermic needle could be used to extract some of the filling material. Were this to be done, however, it would have to be done before there has been significant ingrowth.

While it is believed that breast augmentation and breast reconstruction are the fields in which the present invention will likely find its most immediate utility, this invention is not limited to such uses. For example, implants in accordance with the present invention could be used to build up portions of a person's face, arms, thighs or buttocks. In fact, an envelope made in accordance with this invention could be implanted into any soft tissue in the body.

It will readily be apparent to those skilled in the art that numerous modifications, alterations and changes can be made without departing from the inventive concept described herein. Accordingly, all such variants should be viewed as being within the scope of the invention as set forth in the claims below.

What is claimed is:

1. A method of breast augmentation comprising the steps of:

providing a soft tissue implant comprising an outer membrane formed into a closed pouch and a filling material contained in the closed pouch, the filling material comprising comminuted collagen and elastin, in which a natural tissue structure has been broken up, wherein the collagen is not cross-linked; and implanting into the breast the soft tissue implant.

2. The method of claim 1 further comprising the step of changing the size of said implant after implantation thereof by injecting or removing said filling material into said pouch through an hypodermic needle.

3. A method of making a soft tissue implant pouch containing filling material wherein said pouch is made of a membrane derived from natural animal membrane selected from the group comprising the peritoneum, omentum, amnion, chorion, pleura, pericardium, facia lata, dura mater, intestine and dermis and wherein said filling material is derived from a starting material selected from the group comprising animal ligaments, membranes and tendons, said method comprising treating said natural animal membrane, treating said filling material before, after or simultaneously with treating said natural animal membrane, forming said treated animal membrane into a partially closed pouch, placing said treated filling material into said partially closed pouch and then closing the rest of the pouch.

4. The method of claim 3 wherein said natural animal membrane is treated using a process comprising the steps of washing said membrane in water, treating the washed membrane with a strong alkali, treating said membrane with an acid, and treating said membrane with a base to neutralize the acid.

5. The method of claim 4 further comprising the step of drying said membrane after said neutralizing step.

6. The method of claim 3 wherein said filling starting material is treated using a process comprising the steps of treating said starting material with a strong alkali solution, treating the starting material with an acid, treating the starting material with a base to neutralize the acid, and mechanically working the starting material to separate the elastin fibers.

7. The method of claim 6 further comprising the step of drying said filling material after said neutralizing step.

8. The method of claim 6 wherein said starting material is bovine ligamentum nuchae.

9. The method of claim 3 wherein said pouch membrane is prepared by a process according to claim 4 and said filling material is prepared by a process according to claim 6.

10. The method of claim 3 wherein said pouch is made by sewing together two pieces of treated natural animal membrane around the periphery of said pouch.

11. The method of claim 3 wherein said pouch is made of a single piece of treated natural animal membrane which has been folded and sewn around the periphery of said pouch.

* * * * *